United States Patent [19]

Suda

[11] Patent Number: 5,527,470
[45] Date of Patent: Jun. 18, 1996

[54] WATER QUALITY MONITORING AND CONTROL SYSTEM FOR AN ICE MAKER

[75] Inventor: Richard Suda, Lisle, Ill.

[73] Assignee: Everpure Inc., Westmont, Ill.

[21] Appl. No.: 340,260

[22] Filed: Nov. 16, 1994

[51] Int. Cl.[6] .............................. B01D 17/12; F25C 1/00
[52] U.S. Cl. .............................. 210/739; 62/75; 62/126; 62/135; 62/348; 210/96.1; 210/743; 324/439
[58] Field of Search ...................... 210/85, 96.1, 198.1, 210/205, 743, 746, 143, 739; 137/2, 5, 93; 62/125, 126, 152, 151, 177, 231, 348, 66, 75, 340, 348, 135; 324/439, 446, 442, 443

[56] References Cited

U.S. PATENT DOCUMENTS

| | | | |
|---|---|---|---|
| 2,775,100 | 12/1956 | Howe | 62/348 |
| 2,983,109 | 5/1961 | Lesson | 62/348 |
| 3,233,417 | 2/1966 | Soderberg | 62/348 |
| 3,361,150 | 1/1968 | Horner | 210/746 |
| 3,484,805 | 12/1969 | Lorenz | 324/439 |
| 3,592,212 | 7/1971 | Schlieimer | 210/746 |
| 5,002,658 | 3/1991 | Isaacs | 62/540 |
| 5,239,836 | 8/1993 | Sakai | 62/348 |
| 5,374,380 | 12/1994 | James | 324/439 |

*Primary Examiner*—Joseph W. Drodge
*Attorney, Agent, or Firm*—Greer, Burns, & Crain, Ltd.

[57] ABSTRACT

A method for monitoring and controlling water quality in a water phase changing device, such as an ice maker, having a water inlet, a water outlet, a reservoir configured for retaining a supply of water and being in fluid communication with the inlet and the outlet, and a flow controller for controlling the flow of water into the device, such as an ice maker, includes the steps of monitoring TDS concentration of water retained in said reservoir, and actuating at least one of a water input controller and a water dump controller to adjust the composition of the water in the reservoir when the monitored TDS concentration exceeds a preset TDS target concentration.

13 Claims, 4 Drawing Sheets

WATER QUALITY MONITORING AND CONTROL SYSTEM FOR AN ICE MAKER

BACKGROUND OF THE INVENTION

The present invention relates to water quality monitoring and control systems for use in devices wherein the phase of the water changes, such as ice makers, steamers, freezers, and/or humidifiers, and specifically relates to a system for operating such devices to maximize efficiency in the use of water and power.

Conventional devices which cause phase changes in water, including but not limited to ice makers, freezers, steamers and/or humidifiers, typically suffer from water-caused maintenance problems. For example, approximately 60% of maintenance costs on commercial ice making equipment are caused by water. Perhaps the greatest cause of equipment failure in ice making and steaming equipment is water-borne dissolved minerals commonly referred to as Total Dissolved Solids (TDS), measured in parts per million (ppm). Unacceptably large concentrations of TDS interfere with machine operation while in solution, and form deposits of unwanted scale when the water changes phase.

While in solution, excessive TDS concentrations can prevent the formation of ice cubes and produce undesirable cloudy appearing ice cubes. Scale deposits cause clogging of water lines, put additional loading on the pump, and act as an insulator which prevents the extraction of heat from the water. Harvesting of ice cubes becomes difficult in severely scaled ice makers as the formed cubes often become stuck to the evaporator plate, and eventually may damage the evaporator plate.

Further, in some cases, as TDS builds up in an ice maker, the pH of the water also increases, which decreases the ability of minerals to stay in solution. Thus, left unchecked, the scale forms progressively faster.

Conventional ice makers address the problem of TDS buildup by periodically flushing the water lines and other components during the harvest phase of the cube formation cycle. In addition, the storage sump, which retains a supply of chilled water recirculated to form ice cubes, is also emptied at this time, either partially or totally. Although effective in controlling TDS levels, these conventional procedures are extremely wasteful.

Specifically, water at ambient temperature must be purchased and directed to the sump, often filtered just prior to reaching the device, and power is expended to chill it to approximately 32° F. Aside from the expense in obtaining the filtered, chilled water, in many areas there is also a sewer tax or other disposal expense which the commercial water user must pay to dispose of the flushed sump water. Considering that typical commercial ice makers operate continually on a cycle time of 18–25 minutes per cycle, and taking into account that large restaurant chains have multiple facilities each with at least one ice making machine, the total expenditure in water and power to remove excess TDS is quite significant. For example it has been estimated that a conventional ice making machine, operating continually, consumes approximately $2,800 worth of electricity and $300 worth of water on an annual basis.

In addition to the power and water costs, the service costs for removing scale from such equipment are significant. The de-liming or acid cleaning used to remove scale has also been found to deteriorate the corrosion-resistant coating, and otherwise shortens the working life of pumps and other expensive components.

Although the above discussion relates primarily to ice makers, similar problems occur with commercial steamers, wherein a supply of stored water is heated to form steam. On steamers, the scale forms on the heating surfaces as the water vaporizes, decreasing thermal efficiency and requiring more power to obtain required temperature levels. Also, related problems occur with humidifiers and commercial shaved ice makers.

Other attempts to decrease TDS and scaling in the water supply of ice makers, steamers and other water phase changing devices include the use of more effective filters and the addition of feed phosphates or acidulents to stop the buildup of minerals. Although filtration is effective in substantially reducing suspended particles, the ionic particles in solution in the water are not significantly reduced. One benefit of filtration is that it will prolong the service interval of ice making machinery. The addition of phosphates or acid to filtered water has also been found to further prolong the service interval as compared to filtration alone. The chemical additives assist in maintaining the ionic particles in solution longer. However, users of such equipment have still been forced to dump excessive amounts of chilled water from their units.

It has been known in the case of commercial steamers, which use significantly less water than do ice makers, to electronically and remotely monitor TDS content of treated water, and to provide a warning signal when TDS concentration exceeds preset limits. The warning signal indicates to the operator that the replaceable demineralizing cartridge must be changed. Such present systems, however, do not have sufficient capacity to operate and reduce the amount of chilled water which is periodically dumped from commercial ice making equipment, or of coordinating the consumption of water with the TDS concentration.

Another drawback of conventional water phase changing equipment is that the rate of scale buildup varies with the varying TDS concentration in different types of water sources, the level of water treatment, and the geographic region. It is also known that pH of water influences the TDS scaling effect of various concentration levels. However, conventional water phase changing equipment is incapable of coordinating control of pH with control of TDS and scaling.

Accordingly, it is an object of the present invention to provide an improved system for monitoring and controlling water quality in a water phase changing device to minimize the undesirable effect of TDS levels, and maximizing the efficiency of the use of water and power.

It is another object of the present invention to provide an improved system for monitoring and controlling a water phase changing device in which treated water is expelled and/or fresh water is introduced on an as needed basis as a function of a monitored TDS concentration to maintain the TDS concentration within preset limits.

It is yet another object of the present invention to provide an improved system for monitoring and controlling water quality whereby water-caused service intervals are substantially extended over conventional systems.

Still another object of the present invention is to provide an improved system for monitoring and controlling water quality in a water phase changing device wherein the pH is monitored and controlled to suit the water conditions of a particular installation.

SUMMARY OF THE INVENTION

Accordingly, the above-listed objects are met or exceeded by the present water quality monitoring and control system, wherein the TDS of recirculating water is periodically monitored. When the TDS reaches a preset threshold, at least a portion of the residual water is expelled from the sump, and additional water is added to the existing recirculating water on an as needed basis to decrease the TDS concentration. The majority of residual treated (chilled or heated, filtered, phosphate added) water is maintained in the system as long as possible until the maximum acceptable TDS concentration is achieved. A feature of the present system is that treated water is not dumped as frequently as in conventional devices. Thus, significant savings in power and water consumption may be realized over conventional devices. As an option, a pH sensor may be added to the system for monitoring the pH level of the water in the device. An acidulent injector connected to the pH sensor and to the controller may be arranged to inject acidulent as needed into the water to maintain pH within desired ranges.

More specifically, the present invention provides a method for monitoring and controlling water quality in a water phase changing device having a water inlet for receiving an inflow of water, a reservoir in fluid communication with the inlet and containing a supply of recirculating water, and a water outlet for expelling the water. The method includes monitoring the TDS concentration of the recirculating water in the device; and controlling at least one of the inflow of water into the device and expulsion of water from the outlet of the device as a function of the monitored TDS concentration for maintaining TDS within a preset concentration limit.

In another embodiment, the present method for monitoring and controlling water quality is suitable for use in a water phase changing device having a water inlet, a water outlet, a reservoir configured for retaining a supply of water and being in fluid communication with the inlet and the outlet, and a flow controller for controlling the flow of water into the device. The method includes the steps of placing a TDS probe in operational relationship with the water in the phase changing device; connecting the TDS probe to a control unit for controlling the flow control device; providing the control unit with a preset TDS target concentration; monitoring TDS concentration of the water in the device with the TDS sensor; and actuating the flow controller to perform at least one of introducing additional water into the reservoir and dumping excess existing water when the monitored TDS concentration exceeds the preset TDS target concentration. As stated above, it is contemplated that the water phase changing device may be an ice making machine, a steamer, a humidifier or equivalent device.

In yet another embodiment, the present invention provides a system for monitoring and controlling water quality in a water phase changing device having a water inlet, a water outlet, a reservoir in fluid communication with the inlet and the outlet for retaining a supply of water, and a flow controller for controlling the flow of water into the device. The system includes a TDS sensor disposed in operational relationship with the water in the phase changing device for monitoring TDS concentration of the water. A control unit is connected to the TDS sensor and to the flow controller for controlling the flow controller. The control unit is provided with target upper and lower TDS concentrations, and is constructed and arranged to actuate the flow controller upon the TDS concentration exceeding the preset limit to perform at least one of introducing water into the device and dumping excess existing water until the TDS concentration reaches the lower target TDS concentration.

DESCRIPTION OF THE PREFERRED EMBODIMENT

Figure 1:
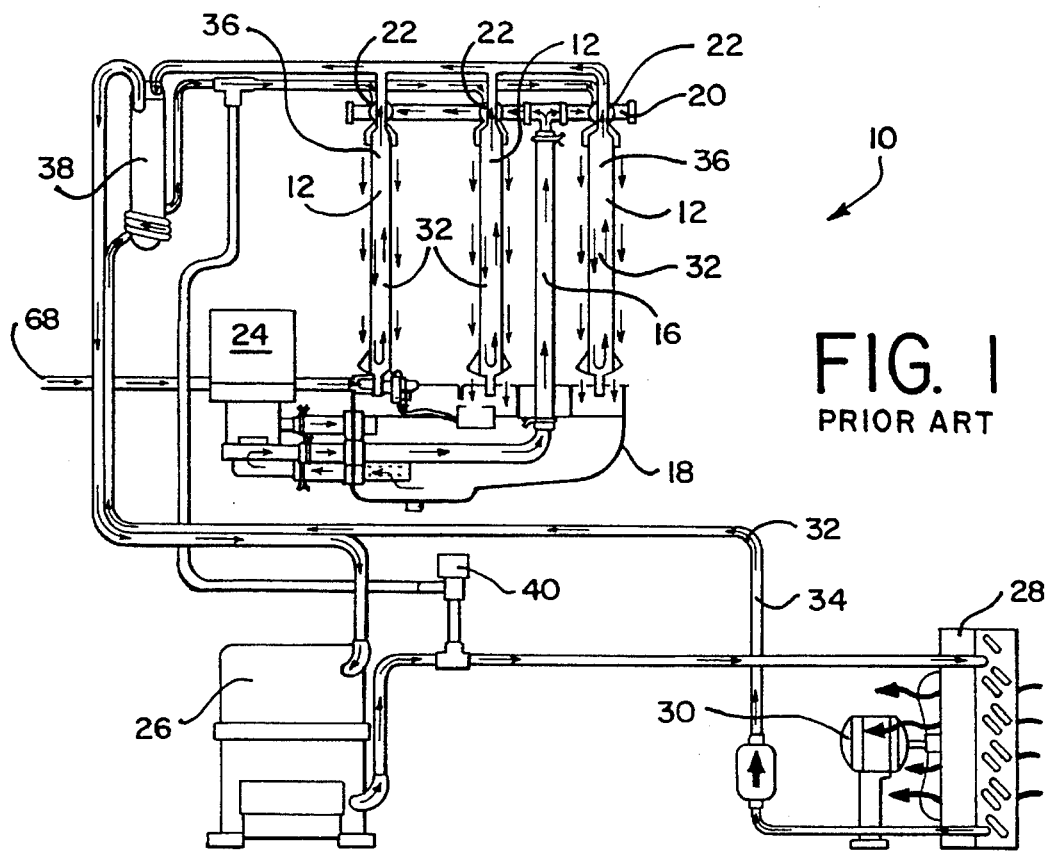
FIG. 1 is a schematic view of a conventional ice making machine of the type suitable for use with the present system, the machine being in the freezing phase of the production cycle.
Figure 2:
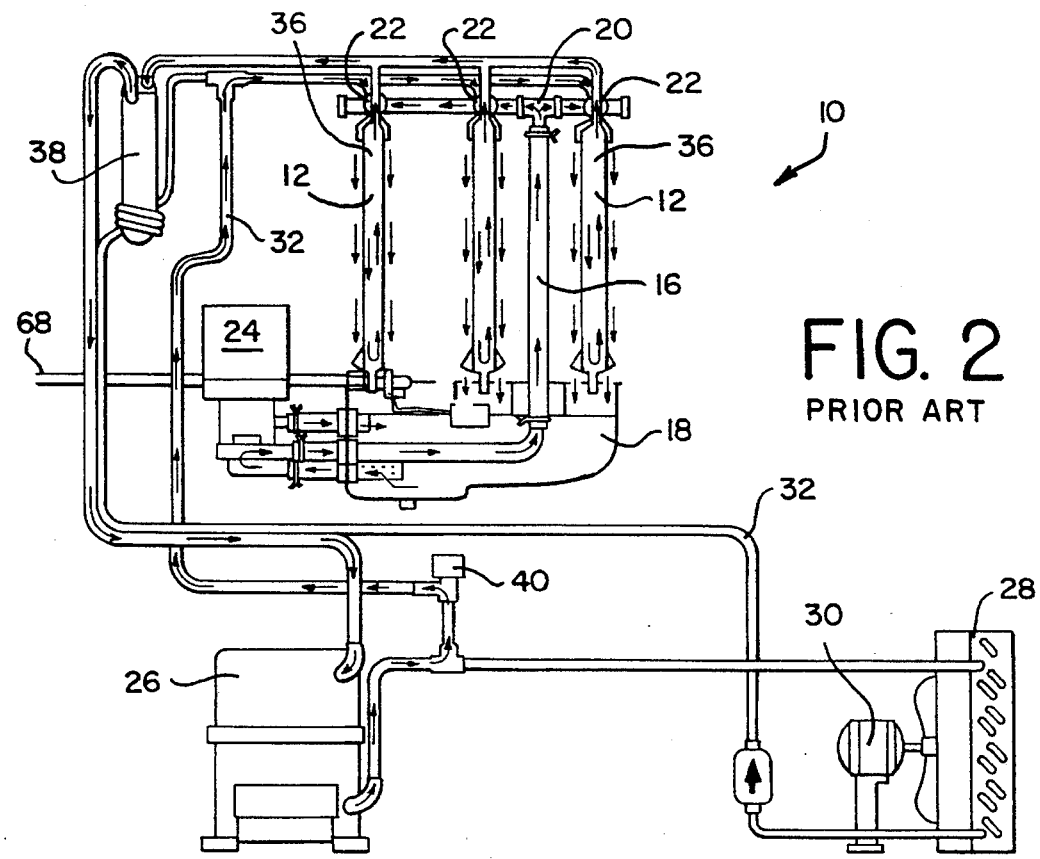
FIG. 2 is a schematic view of a conventional ice making machine of FIG. 1 shown in the harvest phase of the production cycle.

Referring now to the drawings, FIGS. 1 and 2 schematically depict the major components of a commercial ice making machine. Machines of this type are used in restaurants, hotels, fast food outlets, and similar establishments. Basically, these machines operate to change water into ice. However, the principles of the present invention are not restricted to such machines, or even to other types of ice making machines, but may also be applied to steamers, humidifiers and other devices which change water to and/or from other phases.

Figure 3:
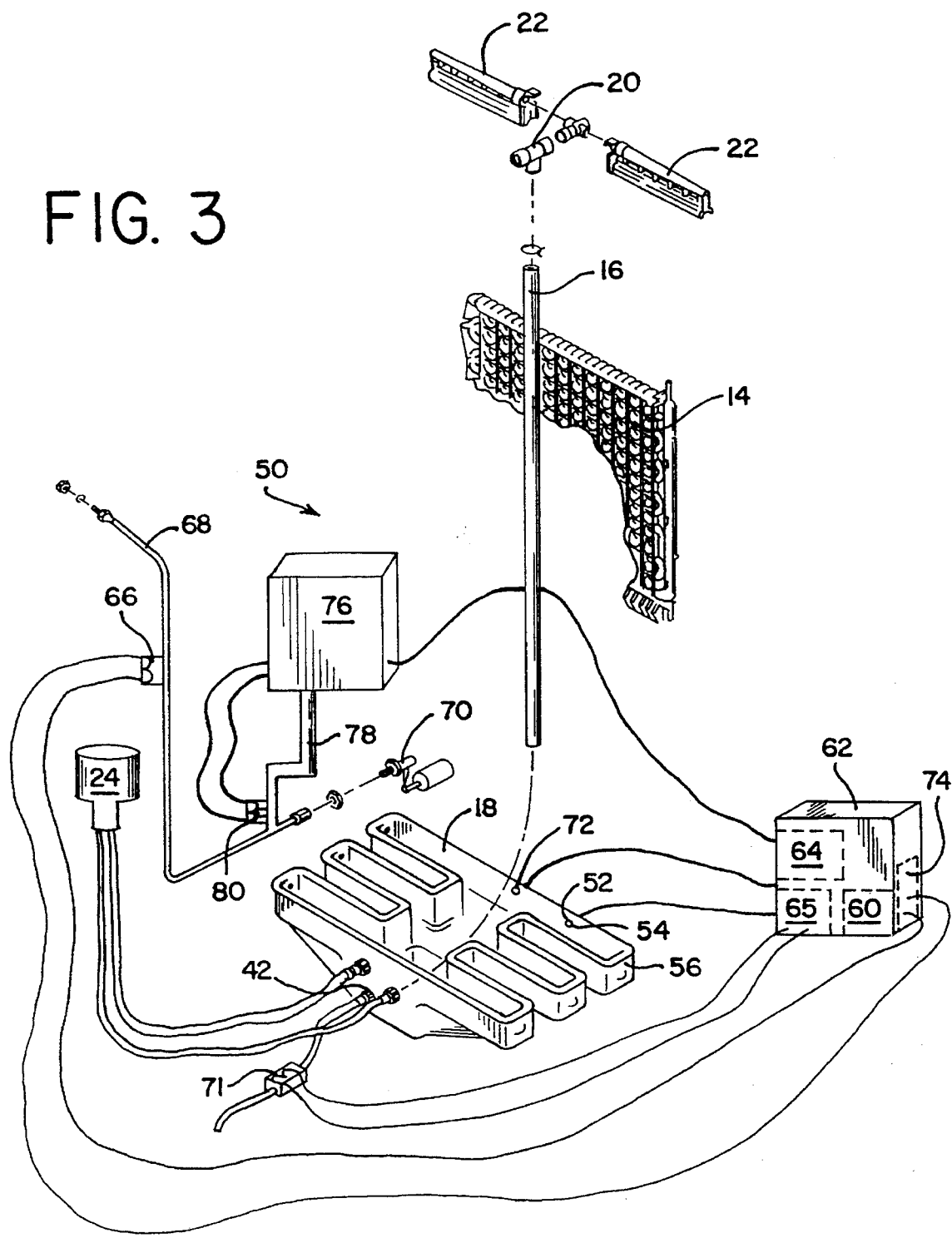
FIG. 3 is a schematic view of an ice making machine equipped with the present system.

More specifically, and referring now to FIGS. 1 and 3, a commercial ice making machine or ice maker is generally designated 10. The machine 10 includes a plurality of evaporator plates 12, each of which is provided with a plurality of generally cuboidal shaped recesses 14 arranged in vertical rows (best seen in FIG. 3). Water is pumped through a feed conduit 16 from a previously filled sump or reservoir 18 through a manifold 20 to a plurality of water distributors 22. Each water distributor 22 has a plurality of openings for distributing water in a cascading fashion down the faces of the recesses 14. At the lower ends of the evaporator plates, the water returns to the sump 18, where it is pumped back up the feed conduit 16 by a pump 24. Water taken up through the conduit 16 and the manifold 20 and used to form ice will be generally compensated for by the addition of small amounts of fresh water to the sump 18.

In a freezing phase of the ice formation cycle, ice cubes are formed in each of the recesses 14 by chilling the evaporator plates 12. This chilling is accomplished by a compressor 26, which compresses gaseous refrigerant and discharges it into a condenser 28 as a high temperature, high pressure gas. A fan 30 is used to assist the operation of the condenser, as is known in the art.

Next, using either air or water, the refrigerant, represented by the arrows 32, is cooled and condensed into a high pressure, medium temperature liquid, which is then passed through a capillary tube 34, where the temperature and pressure of the liquid refrigerant are lowered. At this time, the refrigerant is introduced to interior chambers 36 defined by the evaporator plates 12.

Once in the evaporator plates 12, the refrigerant cools the cascading water, at the same time it becomes warmer through the interaction with the water. As it warms, the refrigerant begins to boil off and become a gas, which is stored in an accumulator 38. The gaseous refrigerant eventually makes its way to the compressor 26, where the cycle is repeated. The continual cascading of water over the chilled recesses 14 causes ice cubes to form in the recesses. The size of the ice cubes is monitored by a cube size control bulb or equivalent device (not shown), which keeps the ice maker operating in the freezing phase of the ice cube formation cycle until the desired size of cubes is reached.

Referring now to FIG. 2, at a predetermined signal, either triggered by ice cube size or a time interval, the ice maker 10 is switched from the freezing phase to a harvest phase, where the formed cubes are collected. Basically, in the harvest cycle, the evaporator plates are warmed slightly to cause the cubes to melt at the contact surface of the recesses 14. The continual cascading of water facilitates the release of the cubes. When sufficient melting has occurred, the cubes will fall from the evaporator plates 12 into a storage bin (not shown), as is known in the art.

More specifically, the evaporator plates 12 are warmed by the diversion of high pressure, high temperature refrigerant from the compressor 26 away from the condenser 28 by the actuation of a gas solenoid valve 40. Thus, the refrigerant is passed from the compressor 26 through the plates 12 and back to the compressor. Once the cubes are harvested, the ice maker 10 is switched by a timer or a physical signal to the freeze phase of the cycle, for the formation of more cubes. Many conventional ice makers 10 have a cube inventory control mechanism, which stops cube production when the storage bin is full.

Referring now to FIG. 3, a major problem of such conventional ice making machines is that through the freezing of the cubes and the repeated recirculation of the chilled water, the Total Dissolved Solids (TDS) concentration of mineral particles increases in the water retained in the sump 18. As the TDS concentration increases, the minerals will begin to be deposited on various components of the ice maker 10 as scale. These components include the recesses 14, the water distributors 22 and various connecting lines. Excessive scale buildup will plug the openings in the water distributors 22, will make the ice cubes cloudy, and will interfere with the transfer of heat in the formation of the cubes themselves.

Water chemists commonly use the Langelier Saturation Index (LI) to measure a solution's ability to dissolve or deposit calcium carbonate, or more specifically, the corrosivity of water. The LI is defined as the difference between the actual or measured pH and a calculated pH or $pH_s$. The calculated $pH_s$ is dependent upon several factors relating to the quality of the water, such as temperature, ionic strength, calcium hardness and total alkalinity of the water.

Through application of the LI, it is known that as the pH of the water increases, the ability of minerals to stay in solution decreases. As such, scale forms faster in water having relatively higher pH.

Conventional ice machines only vaguely or crudely incorporate the principles of the LI by periodically dumping the sump contents after each cycle. Although this procedure lowers the TDS of the recirculating water, it wastes energy by dumping water which has consumed power to chill to approximately 32° F. and also wastes the water itself, which is dumped down the drain. The sump water may be ejected through outlet port 42 (best seen in FIG. 3), although it is contemplated that in some models of ice makers, the sump water is ejected by adding fresh water, causing the sump to overflow into a drain.

Accordingly, the present system, generally designated 50, controls the buildup of TDS and the resulting unwanted scale without dumping excessive amounts of chilled water. Included in the system 50 is a TDS sensor, which includes a probe portion 52 placed in operational contact with the chilled recirculating water, such as through an opening 54 in a sidewall 56 of the sump 18. Alternately, the TDS probe 52 may be draped over the rim of the sump to contact the water, and secured in a conventional manner. The TDS probe 52 is electrically connected to a resistivity/conductivity switch or TDS meter 60. A suitable device is manufactured by McNab, Mount Vernon, N.Y. under Part Nos. 18940 and 18950. It is contemplated that other equivalent components may be utilized to monitor TDS.

Figure 4:
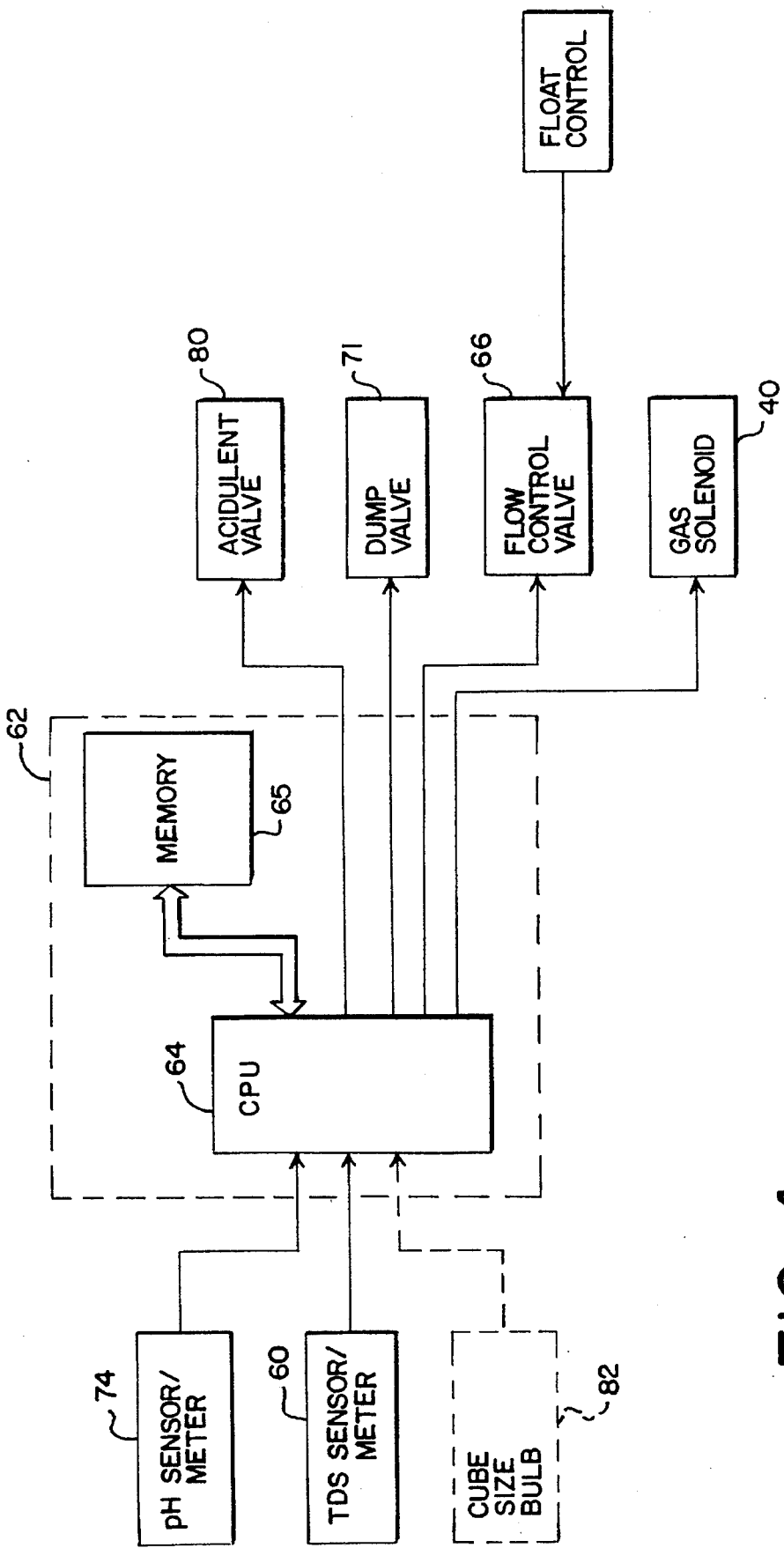
FIG. 4 is an enlarged schematic of the control unit used with the system depicted in FIG. 3.

Referring now to FIGS. 3 and 4, in the preferred embodiment, the conductivity switch 60 (shown hidden) is connected to, and preferably incorporated within a central control unit 62, which also includes a central processing unit 64 (shown hidden) and associated memory 65 such as ROM or RAM. The control unit 62 is also electrically connected to a water flow control valve 66 located in a water inlet supply conduit 68. The valve 66 is preferably the solenoid type. The construction and operation of the valve 66 may vary with the manufacture of the ice maker 10. Water at ambient temperature is introduced into the sump 18 through the inlet conduit 68. In some commercial ice makers, a float valve 70 regulates the inflow of water into the sump to prevent overflowing. In others, the feed water is regulated by the valve 66. In addition, a dump or expulsion valve 71 is used in some models to control the expulsion of water from the sump 18, and is connected to a drain (not shown). As is the case with the valve 66, the dump valve 71 is preferably a solenoid-type valve. The water flow control valve 66 and the dump valve 71 may be collectively referred to as the flow controller.

An important feature of the present system 50 is that the control unit 62 uses the TDS probe 52 and the meter 60 to control the flow controller valve 66 and the dump valve 71 so that the TDS level of the sump water may be accurately controlled. When TDS concentration exceeds preset amounts, the dumping or expulsion of the sump water is triggered and/or fresh water at ambient temperature is introduced into the sump 18. Residual water in the sump which has an excessively high TDS concentration may be expelled from the sump out the dump valve 73. This may be accomplished in at least two ways.

First, the control unit 62 may be programmed to periodically monitor the TDS meter to determine the TDS concentration of the sump water as sensed by the TDS sensor 58. A timing routine may be used so that the control unit 62 monitors the TDS sensor 52 at the end of every cube formation cycle upon completion of the harvest phase. Alternately, monitoring may occur on a timed frequency, such as every 15 minutes. In this scenario, the control unit 62 is programmed to have a high TDS preset level, which in the preferred embodiment may be as high as 2000 ppm. This upper limit will vary depending on the location, the source water, and the particular application. Then, the control unit 62 is programmed so that the sump 18 will be dumped (i.e., the dump valve 71 opened) only upon the TDS probe 52 and meter 60 reading a concentration beyond the preset limit.

Upon the dumping of all or part of the residual water in the sump, the dump valve 71 is closed, and, depending on the type of ice maker, either the flow control valve 66 or the float control valve 70 introduces water into the sump. Both valves 66 and 70 are normally not found in one ice maker 10. If the flow control valve 66 is used to control the inflow of water, the control unit 62 may be used to determine when the valve is closed to prevent overflow of fresh water in the sump 18. It can be made to work in conjunction with the level control device (not shown) already in the ice maker 10.

Alternately, the float valve 66 may be controlled to stop the inflow of water into the sump 18 upon the attainment of a preset TDS level. Such a TDS level is lower than the dump signalling TDS level. This lower TDS level may vary with the application and is contemplated as being on the order of 1,000 ppm or less.

Another way in which TDS concentration may be monitored and controlled using the present system is to monitor the TDS concentration at shorter intervals, while keeping the flow control valve 66 open at least a slight amount at all times. In the event the TDS concentration exceeds a preset level, the flow control valve 66 is temporarily opened wider to increase the volume of ambient water introduced into the sump. Once the monitored TDS concentration falls within the preset limit, as measured by the TDS probe 52, the control unit 62 signals the valve 66 to resume its prior setting.

In ice makers having a mechanical float valve 70, once the dump valve 71 closes or equivalent structure stabilizes the water level in the sump, upon dumping the sump, the float valve 70 opens, introducing fresh water into the sump. Then, as make up water is needed during the ice making cycle, the float valve allows a certain amount of water to trickle into the sump 18.

In addition, in some locations, the characteristics of the source water may require that the pH be monitored to optimize the operation of the device 10. In other words, pH should be maintained at a level which maximizes the retention of minerals in the dissolved state and prevents them from coming out of solution to form scale. In the preferred embodiment, the pH is set at 8, however, depending on several factors relating to water quality, this pH level may be varied. Any pH value less than the preset value will be satisfactory for operation of the ice maker. At higher pH values, the water may not be able to hold satisfactory amounts of ionic minerals in solution, thus scaling will increase.

Referring now to FIG. 3, to adjust pH in the present system 50, a pH probe 72 is placed in operational relationship to the water in the sump 18. As was the case with the TDS probe 52, the pH probe may be mounted in the sidewall 56 of the sump, or may alternately be draped over the sump wall to contact the water. The probe 72 is electrically connected to a pH meter 74 (shown hidden), which is preferably incorporated into the control unit 62. A variety of conventional pH probes and meters are acceptable in the present system 50. An example of a suitable pH meter is manufactured by Signet Scientific, El Monte, Calif. under the Model Nos. MK 700 and MK 800 Series.

In addition to monitoring the pH, the present system 50 may also alter the pH level of the water by adding an acidulent or other chemical additive through an acidulent injector 76. The acidulent injector 76 may be placed in fluid connection with the supply line 68 through a conduit 78 as illustrated, or may be introduced directly into the sump, as desired. A control valve 80 preferably of the solenoid type, controls the flow of acidulent into the sump 18. The valve 80 is in turn controlled by the control unit 62 via electrical connection.

Referring now to FIG. 4, an enlarged schematic view of the control unit 62 is depicted. The signal inputs include the pH meter 74, the TDS meter 60 and, depending on the model of ice maker, a cube size bulb 82 which indicates when the formed ice cubes are large enough to begin the harvest phase. The signal outputs include the acidulent valve 80, the dump valve 71, the flow control valve 66 and the gas solenoid 40.

Figure 5:
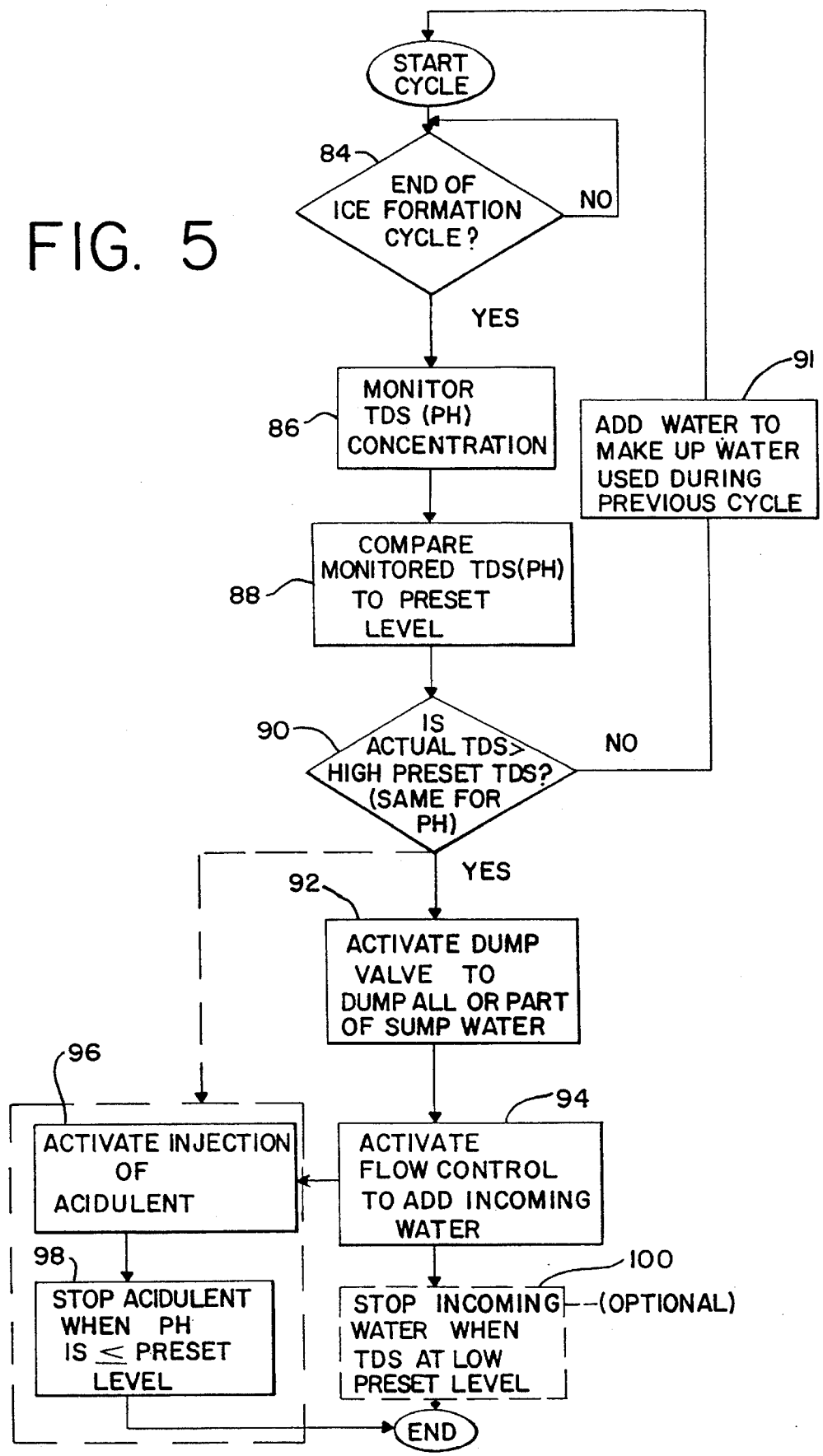
FIG. 5 is a flow chart depicting the present method of controlling a water phase changing device.

Referring now to FIG. 5, a flow chart of how the present system operates is depicted. The illustrated flow chart is to be considered a subroutine which is intended to be added to the overally operational flow chart of the ice making machine 10.

At step 84, the control unit 62 determines whether the harvest phase of the ice making cycle is completed, which may be triggered by a timer or a physical sensor as is known in the art. If the harvest phase is not completed, the routine merely repeats the inquiry at a subsequent time. If the harvest phase is completed, as shown at 86, the control unit 62 monitors the TDS concentration of the TDS meter 52. In systems provided with the pH monitor option, then the pH is monitored as well at this step.

Once monitored, the TDS concentration is compared at step 88 to the preset level, and, similarly, the monitored pH value is compared with its preset level. At step 90, if the actual TDS value is less than the preset value, the routine merely reruns and a new ice making cycle starts with the existing water in the sump plus new water added as at step 91 to make up water used to make ice. However, it should be understood that in some models of ice maker, the make up water is introduced simultaneously with the freezing cycle, and a separate step 91 is then unnecessary. On the contrary, if the actual TDS value exceeds the preset level, it will be seen at step 92 that the dump valve 71 is activated to at least partially drain the sump 18.

At step 94, the control unit 62 activates the flow control valve 66 to introduce fresh water, which typically occurs once the previously existing water in sump 18 is eliminated. If the optional pH system is provided, and it has been determined through monitoring of the pH meter 74 that the pH exceeds 8 or other preset level, step 96 triggers the injection of acidulent in conjunction with the introduction of water into the sump 18. The acidulent is added by the injector 76 until the pH meter 74 obtains a reading at or below the preset level, as shown at step 98. As an option, the incoming water may be stopped upon reaching the lower preset TDS level, shown at step 100.

Under the present system as an example, a sump 18 having a capacity of 3 gallons will be filled upon start up of the machine. After the first cycle, approximately 0.6 gallons (as an example) used during the first cycle to make ice will be added as make up water. This operation will be repeated, and dumping of the sump will be postponed, until TDS exceeds the preset limit, at which time at least a portion of the sump will be dumped.

Thus, it will be seen that the present system 50 improves the efficiency of conventional water phase changing devices. The total amounts of water and power consumed per cycle is significantly reduced due to close monitoring of TDS concentration.

While a particular embodiment of the water quality monitoring and control system for water undergoing phase changes of the invention has been shown and described, it will be appreciated by those skilled in the art that changes and modifications may be made thereto without departing from the invention in its broader aspects and as set forth in the following claims.

What is claimed is:

1. A system for making ice while monitoring and controlling water quality in an ice making device having a water inlet, a water outlet, a reservoir in fluid communication with the inlet and the outlet for retaining a supply of water, an ice sensor for sensing the readiness of the ice for harvest and for periodically triggering an ice harvest, a dump valve for expelling water from the reservoir out the outlet, and a flow controller for controlling the flow of water into the device, said system comprising:

a TDS sensor configured for disposal in operational relationship with the water in the ice making device for monitoring TDS concentration of the water;

a control unit coupled to connections which are operable for connection to the dump valve, the ice sensor, to said TDS sensor and to the flow controller for controlling the flow of water into and out of the device;

wherein said control unit is provided with at least an upper target TDS concentration, and is constructed and arranged to confirm that said ice harvest has been triggered and upon confirmation actuate at least one of the flow controller and the dump valve upon the monitored TDS concentration exceeding said upper target concentration to perform at least one of introducing water into the device and dumping excess existing water, said introduction and/or dumping of water occurring in conjunction with the harvest of the ice.

2. The system as defined in claim 1 further including a pH sensor disposed in operational relationship to the water in said ice making device, and also being connected to said control unit so that when the water in the device exceeds preset pH limits provided to said control unit, said control unit generates a signal.

3. The system as defined in claim 2 further including an acidulent injector constructed and arranged for injecting acidulent into the water of the ice making device, said injector configured for receiving said signal and for injecting acidulent into said water until said pH sensor senses a pH value within said preset limits.

4. The system as defined in claim 1 wherein the device includes a reservoir control mechanism which maintains a level of water in said reservoir independently of the operation of said control unit.

5. The system as defined in claim 1 wherein said reservoir includes a sump assembly.

6. The system as defined in claim 5 wherein said TDS sensor is placed in contact with water in said sump assembly.

7. A method for making ice while monitoring and controlling water quality comprising the steps of:

providing an inflow of water to an ice making device having a water inlet for receiving the inflow of water, a reservoir in fluid communication with the inlet and containing a supply of recirculating water and a water outlet for expelling at least a portion of the recirculating water, said device constructed and arranged to recirculate said water between said reservoir and at least one evaporator component;

chilling and freezing a portion of the recirculating water to make a supply of ice on said evaporator component for harvesting on a cyclical basis;

monitoring the TDS concentration of the recirculating water in the device at least as often as each harvest cycle;

establishing a preset upper acceptable TDS concentration; and controlling the TDS concentration of said harvested ice and said recirculating water by controlling at least one of the receiving of inflow water into the device and the expelling of a portion of the recirculating water out of the outlet of the device, during each said harvest cycle, as a function of the monitored TDS concentration for maintaining the TDS concentration below said preset upper concentration while minimizing the volume of expelled recirculating water.

8. The method as defined in claim 7 further including providing a flow controller for controlling the inflow of water to the device, and activating said flow controller to stop the inflow of water into the device when said TDS concentration reaches a preset lower limit.

9. The method as defined in claim 8 wherein said preset lower limit is approximately 1000 ppm or less.

10. The method as defined in claim 7 further including the steps of:

providing a flow controller for controlling the inflow of water to the device;

calibrating said flow controller to continually introduce a specified volume of additional water; and changing the volume of water introduced into said flow controller when said TDS concentration deviates from said preset value.

11. The method as defined in claim 7 further including placing a pH sensor in operational relationship with the water in the ice making device.

12. The method as defined in claim 11 further including providing an acidulent injector for injecting acidulent into the water of the ice making device, and connecting said injector to said device so that acidulent is injected into the water when the pH exceeds a preset value.

13. The method as defined in claim 7 further including establishing a preset lower TDS concentration, and controlling at least one of the inflow of water into, and the expelling of water from the device until said lower TDS concentration is achieved and monitored.

* * * * *